(12) United States Patent
Gupta

(10) Patent No.: US 8,095,543 B1
(45) Date of Patent: Jan. 10, 2012

(54) FAST ALGORITHMS AND METRICS FOR COMPARING HIERARCHICAL CLUSTERING INFORMATION TREES AND NUMERICAL VECTORS

(75) Inventor: Anjum Gupta, La Jolla, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 828 days.

(21) Appl. No.: 12/183,926

(22) Filed: Jul. 31, 2008

(51) Int. Cl.
*G06F 17/00* (2006.01)

(52) U.S. Cl. ........ 707/749; 707/750; 707/754; 707/758; 707/778

(58) Field of Classification Search .................. 707/749, 707/750, 754, 758, 778
See application file for complete search history.

(56) References Cited

U.S. PATENT DOCUMENTS

| | | | | |
|---|---|---|---|---|
| 6,308,175 | B1 * | 10/2001 | Lang et al. | 707/608 |
| 7,401,087 | B2 * | 7/2008 | Copperman et al. | 707/737 |
| 7,792,770 | B1 * | 9/2010 | Phoha et al. | 706/45 |
| 2007/0083808 | A1 | 4/2007 | Setlur et al. | |
| 2007/0250522 | A1 * | 10/2007 | Perrizo | 707/101 |

OTHER PUBLICATIONS

Stuart Russell "Analogy by Similarity." In David Helman (Ed.), Analogical Reasoning, Boston, MA: D. Reidel, 1988.

* cited by examiner

*Primary Examiner* — Sana Al Hashemi
(74) *Attorney, Agent, or Firm* — Kyle Eppele; J. Eric Anderson

(57) ABSTRACT

In various embodiments, a method for determining a similarity between two data sets is disclosed, the steps of which include determining a first list of data clusters for a first hierarchically-organized data set, determining a second list of data clusters for a second hierarchically-organized data set, and determining a similarity between the first and second data sets by calculating a maximum flow between the first list of data clusters and the second list of data clusters.

12 Claims, 4 Drawing Sheets

FAST ALGORITHMS AND METRICS FOR COMPARING HIERARCHICAL CLUSTERING INFORMATION TREES AND NUMERICAL VECTORS

This invention (Navy Case No. 98993) was developed with funds from the United States Department of the Navy. Licensing inquiries may be directed to Office of Research and Technical Applications, Space and Naval Warfare Systems Center, San Diego, Code 2112, San Diego, Calif., 92152; telephone 619-553-2778; email: T2@spawar.navy.mil.

BACKGROUND

I. Field

This disclosure relates to data mining, machine learning and data management methods and systems.

II. Background

Expert systems and other data-based systems often can be described as programs or systems that contain some subject-specific knowledge having some particular organization. When multiple systems are used to service a common subject, it should be appreciated that a common (but not shared) database may begin to vary from one system to another. Accordingly, it can be important to compare one such database to another from time to time.

However, while conventional approaches to comparing data sets tend to look at commonly shared data, they do not generally take into consideration how such data sets may differ in internal organization. Accordingly, new approaches to data management may be desirable.

SUMMARY

Various aspects and embodiments of the invention are described in further detail below.

In a first series of embodiments, a method for determining a similarity between two data sets includes determining a first list of data clusters for a first hierarchically-organized data set, determining a second list of data clusters for a second hierarchically-organized data set, and determining a similarity between the first and second data sets by calculating a maximum flow of between the first list of data clusters and the second list of data clusters.

In another series of embodiments, an electronic medium capable of being read by a computing device is disclosed. The electronic medium can contain instructions for determining a first list of data clusters for a first hierarchically-organized data set, determining a second list of data clusters for a second hierarchically-organized data set, and determining a similarity between the first and second data sets by calculating a maximum flow of between the first list of data clusters and the second list of data clusters.

BRIEF DESCRIPTION OF THE DRAWINGS

The features and nature of the present disclosure will become more apparent from the detailed description set forth below when taken in conjunction with the accompanying drawings in which reference characters identify corresponding items.

DETAILED DESCRIPTION

The disclosed methods and systems below may be described generally, as well as in terms of specific examples and/or specific embodiments. For instances where references are made to detailed examples and/or embodiments, it should be appreciated that any of the underlying principles described are not to be limited to a single embodiment, but may be expanded for use with any of the other methods and systems described herein as will be understood by one of ordinary skill in the art unless otherwise stated specifically.

Figure 1:
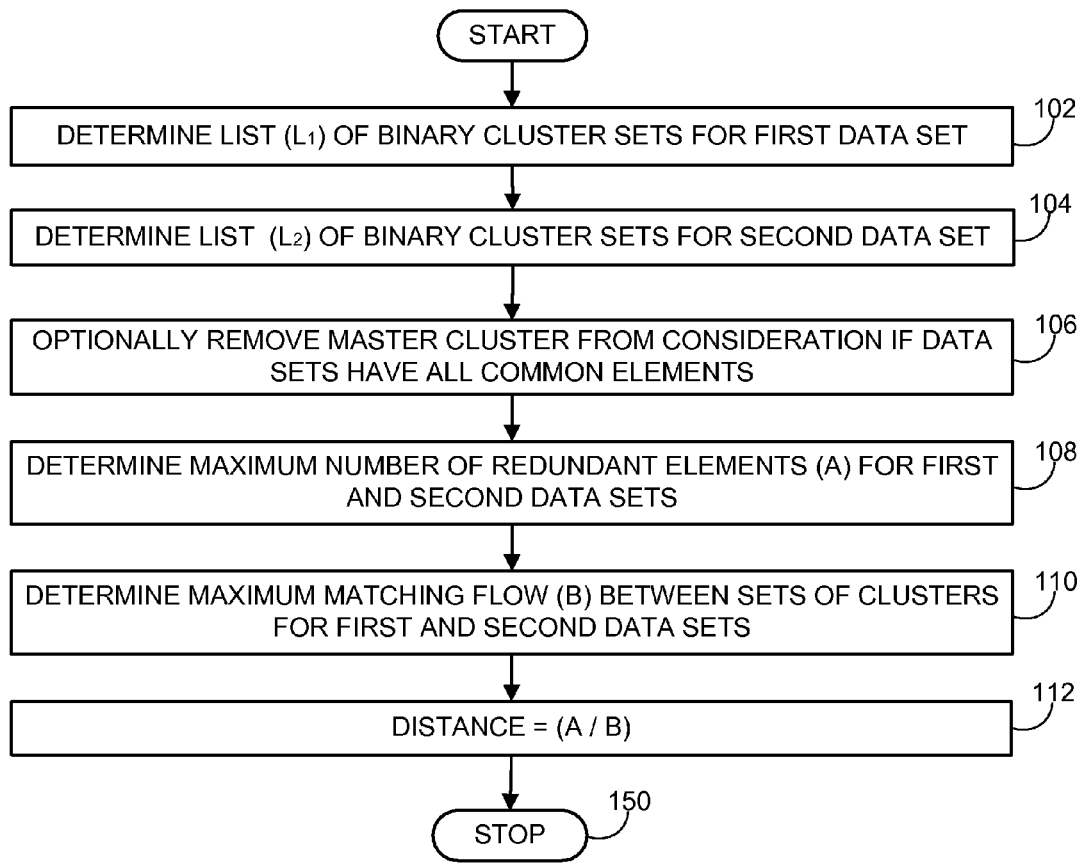
FIG. 1 is a flowchart outlining an exemplary operation of the disclosed methods and systems.
Figure 2:
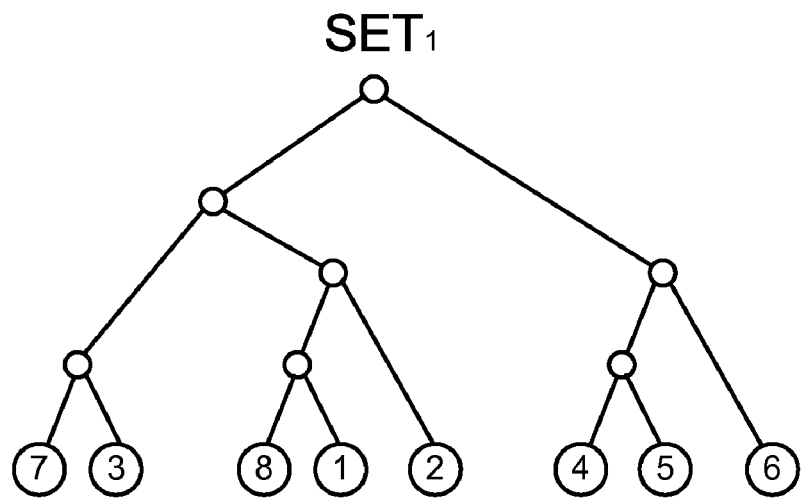
FIGS. 2 and 3 depict two exemplary hierarchical data sets used in the operation of the flowchart of FIG. 1.
Figure 3:
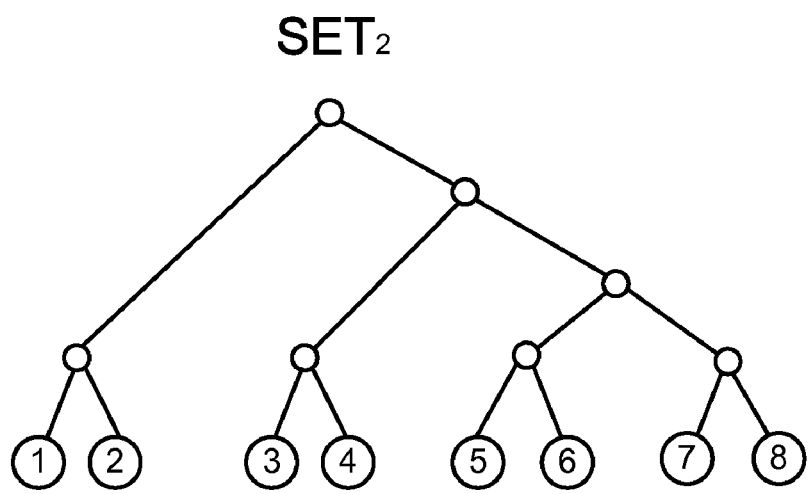

FIG. 1 is a flowchart outlining an exemplary operation of the disclosed methods and systems. For reference in explanation of the disclosed operations, FIGS. 2 and 3 are provided as two exemplary hierarchical data sets used in the operation of the flowchart of FIG. 1. Note that the data sets SET1 and SET2 have a common set of elements data elements (1 ... 8) with a different hierarchical data structure.

Figure 4:
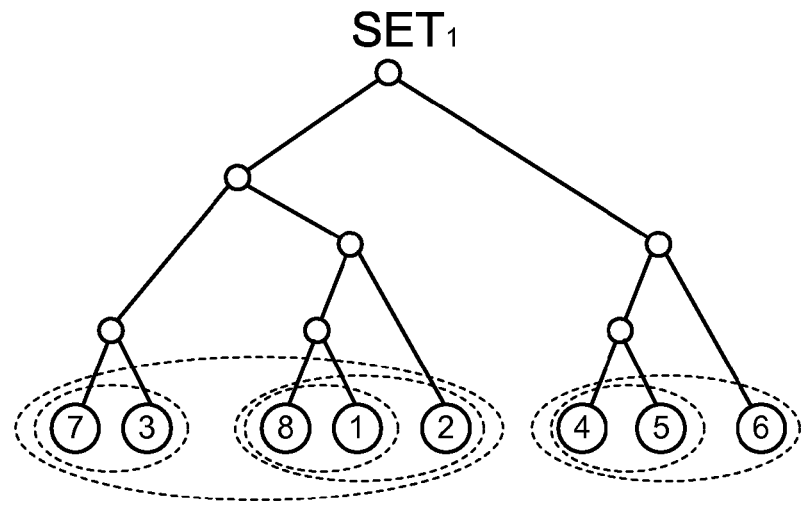
FIGS. 4 and 5 depict the relative hierarchical clustering for the data sets of FIGS. 2 and 3.
Figure 5:
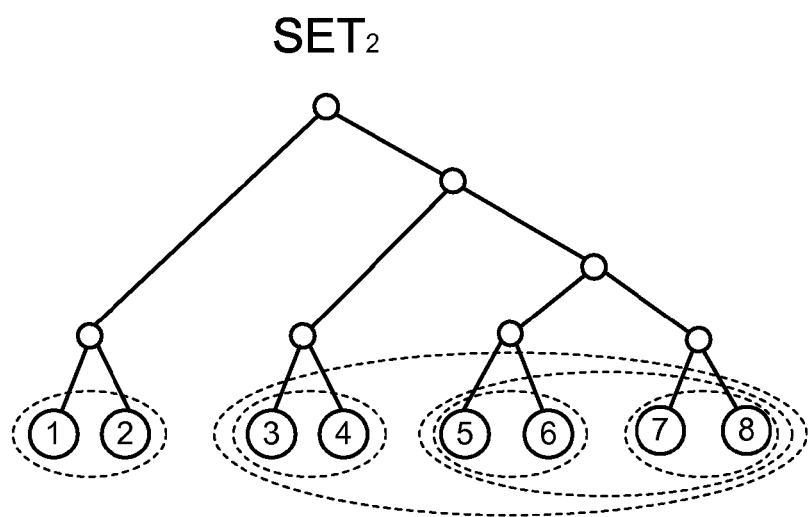

The process starts in step 102 where a first list (L1) is determined for the data set SET1 of FIG. 2. As shown in FIG. 4, the various clusters can be determined based on the binary hierarchical structure data set SET1, and for the present embodiment of SET1 a list of six clusters is developed. Next, in step 104, a second list (L2) is determined for the data set SET2 of FIG. 3. As shown in FIG. 5, the various clusters can be determined based on the binary hierarchical structure data set SET2, and for the present embodiment of SET2 a list of six clusters is also developed. Control continues to step 106.

Control continues to step 106, while every available cluster of each of SET1 and SET2 may be taken into consideration, in various embodiments (such as the present instance) the list of clusters may exclude the "master cluster" of each of SET1 and SET2 given that the list of data elements (1 ... 8) is the same for both sets SET1 and SET2 as such information will not add to the quality of a computational output. However, in embodiments where two data sets do not have identical sets of elements, the respective master clusters may optionally be used in further computation.

Also note that, in various embodiments, it may be useful to cull the available list of clusters. For example, in various embodiments it may be desirable to exclude small clusters below a predetermined minimum size threshold and/or exclude large clusters above a predetermined maximum size threshold. Control continues to step 108.

Figure 6:
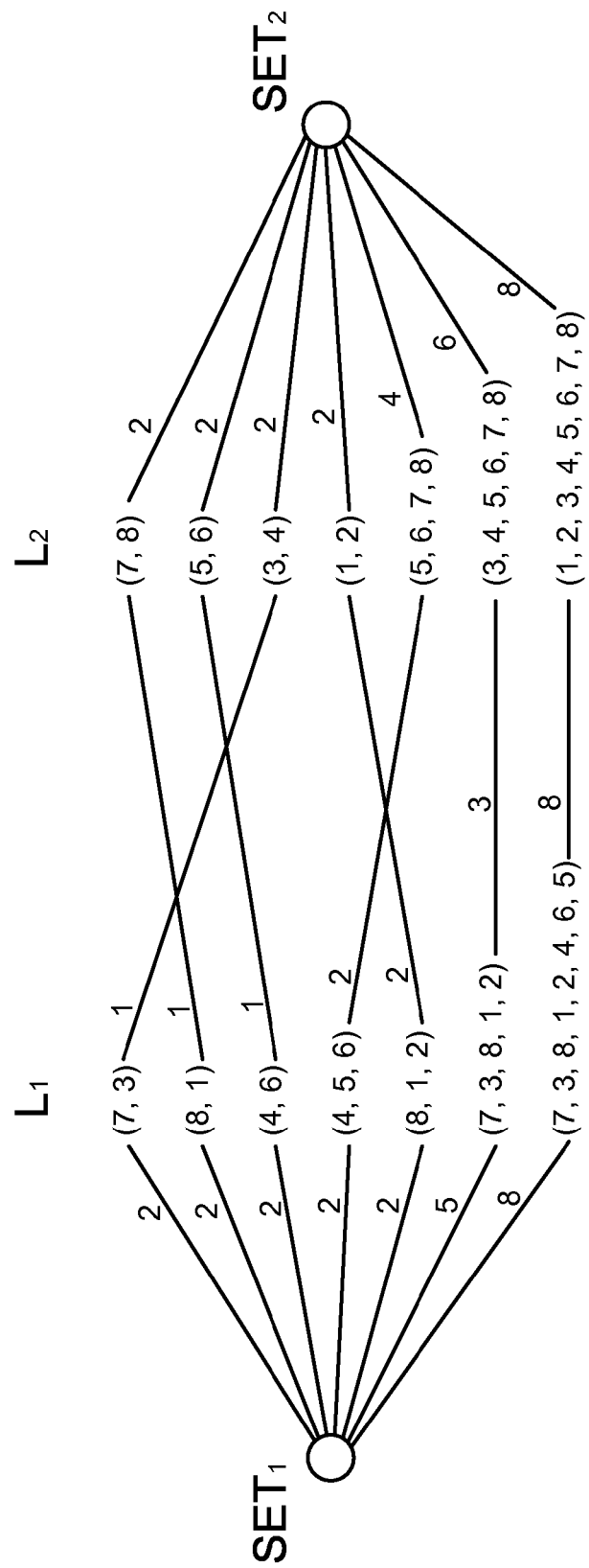
FIG. 6 depicts the data flow between the data sets of FIGS. 2 and 3.

In steps 108-112, a maximum data flow ("max-flow") may be determined between list L1 and list L2, and for these steps attention is directed to FIG. 6, which depicts the data flow between the data sets of FIGS. 2 and 3.

In step 108, a maximum number of redundant elements between clusters of list L1 and list L2 can be determined. As shown in FIG. 6, seven clusters, including master clusters (at bottom of each list L1 and L2) are depicted. Next, in step 110, the cardinalities, i.e., the maximum possible matching flow between the lists of clusters is determined. Then, in step 112, the output of step 108 is normalized by the output of step 110 to determine a matching "max-flow" metric. Control then continues where the process stops.

It should be appreciated that the disclosed operations may be used for a wide variety of purposes where a distance metric may be used for evaluating a distance between two multi-dimensional vectors, or any other entity that can be written as a list of numbers or list of list of numbers. For example, this scheme can be applied to compare two images, two audio streams, two DNA sequences, and the like.

In various embodiments where the above-described systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like.

Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform the above-described systems and/or methods.

For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods related to communications.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method for determining a similarity between two data sets, comprising:
    determining a first list of data clusters for a first hierarchically-organized data set;
    determining a second list of data clusters for a second hierarchically-organized data set;
    removing a master cluster from consideration if the first and second data sets have all common elements;
    determining a similarity between the first and second data sets by calculating a maximum flow between the first list of data clusters and the second list of data clusters;
    determining a maximum number of redundant elements for the first and second data sets; and
    dividing the maximum number of redundant elements by the maximum matching flow to arrive at a distance metric.

2. The method of claim 1, wherein the first list of data clusters includes only a subset of the total available clusters for the first data set.

3. The method of claim 2, the second list of data clusters includes only a subset of the total available clusters for the second data set.

4. The method of claim 2, wherein determining a first list of data clusters includes excluding data clusters having a size below a minimum size threshold.

5. The method of claim 2, wherein determining a first list of data clusters includes excluding data clusters having a size above a maximum size threshold.

6. The method of claim 2, wherein the maximum flow is based upon cardinalities between the first and second data sets.

7. An electronic medium capable of being read by a computing device, the electronic medium containing instructions for:
    determining a first list of data clusters for a first hierarchically-organized data set;
    determining a second list of data clusters for a second hierarchically-organized data set;
    removing a master cluster from consideration if the first and second data sets have all common elements;
    determining a similarity between the first and second data sets by calculating a maximum flow between the first list of data clusters and the second list of data clusters;
    determining a maximum number of redundant elements for the first and second data sets; and
    dividing the maximum number of redundant elements by the maximum matching flow to arrive at a distance metric.

8. The electronic medium of claim 7, wherein the first list of data clusters includes only a subset of the total available clusters for the first data set.

9. The electronic medium of claim 8, the second list of data clusters includes only a subset of the total available clusters for the second data set.

10. The electronic medium of claim 8, wherein determining a first list of data clusters includes excluding data clusters having a size below a minimum size threshold.

11. The electronic medium of claim 8, wherein determining a first list of data clusters includes excluding data clusters having a size above a maximum size threshold.

12. The electronic medium of claim 8, wherein the maximum flow is based upon cardinalities between the first and second data sets.

* * * * *